US010159641B2

(12) United States Patent
Almiñana Doménech et al.

(10) Patent No.: US 10,159,641 B2
(45) Date of Patent: Dec. 25, 2018

(54) FERMENT EXTRACT OF A BACTERIAL STRAIN FOR THE INCREASE OF ADIPONECTIN LEVELS

(71) Applicant: Lubrizol Advanced Materials, Inc., Cleveland, OH (US)

(72) Inventors: Nuria Almiñana Doménech, Barcelona (ES); Antonio Vicente Ferrer Montiel, Alicante (ES); María del Carmen Lidón Moya, Barcelona (ES); Albert Soley Astals, Barcelona (ES); Núria García Sanz, Alicante (ES)

(73) Assignee: LUBRIZOL ADVANCED MATERIALS, INC., Cleveland, OH (US)

( * ) Notice: Subject to any disclaimer, the term of this patent is extended or adjusted under 35 U.S.C. 154(b) by 55 days.

(21) Appl. No.: 15/300,923

(22) PCT Filed: Mar. 30, 2015

(86) PCT No.: PCT/IB2015/052326
§ 371 (c)(1),
(2) Date: Sep. 30, 2016

(87) PCT Pub. No.: WO2015/151009
PCT Pub. Date: Oct. 8, 2015

(65) Prior Publication Data
US 2017/0014334 A1 Jan. 19, 2017

(30) Foreign Application Priority Data

Mar. 31, 2014 (EP) ..................... 14382129

(51) Int. Cl.
| | | |
|---|---|---|
| *A61K 8/99* | (2017.01) | |
| *A61Q 19/08* | (2006.01) | |
| *A61K 9/00* | (2006.01) | |
| *A61K 35/742* | (2015.01) | |
| *A61Q 19/00* | (2006.01) | |
| *C12P 1/04* | (2006.01) | |

(52) U.S. Cl.
CPC .............. *A61K 8/99* (2013.01); *A61K 9/0014* (2013.01); *A61K 35/742* (2013.01); *A61Q 19/00* (2013.01); *A61Q 19/08* (2013.01); *C12P 1/04* (2013.01); *A61K 2800/10* (2013.01); *A61K 2800/74* (2013.01)

(58) Field of Classification Search
CPC .... A61K 8/99; A61K 2800/10; A61K 35/742; A61K 9/0014; A61K 2800/85; A61K 35/74; A61K 8/0208; A61K 9/70; A61Q 19/08; A61Q 19/00; C12P 1/04
See application file for complete search history.

(56) References Cited

U.S. PATENT DOCUMENTS

2003/0003107 A1* 1/2003 Farmer ................ A01N 63/00
424/184.1

FOREIGN PATENT DOCUMENTS

| CN | 101475920 A | * | 7/2009 | |
|---|---|---|---|---|
| CN | 103409348 A | | 11/2013 | |
| CN | 103655437 A | * | 3/2014 | |
| JP | 2010-173991 A | | 8/2010 | |
| WO | WO 92/18637 A1 | | 10/1992 | |
| WO | WO 99/10477 A1 | | 3/1999 | |
| WO | WO 2005/013885 A2 | | 2/2005 | |
| WO | WO 2013002819 A1 | * | 1/2013 | ........... C07D 417/14 |

OTHER PUBLICATIONS

Martinez-Luis et al (Molecules, 2012, vol. 17, pp. 11146-11155).*
Ahmadian et al (Journal of Applied Microbiology, 2007, vol. 103, pp. 1081-1089) (Year: 2007).*
Kerdudo et al (International Journal of Cosmetic Science, 2015, vol. 37, pp. 31-40) (Year: 2015).*
Golbidi, et al. "Exercise Induced Adipokine Changes and the Metabolic Syndrome," J. Diabetes Res., pp. 1-16 (2014).
Petersen, et al., "The anti-inflammatory effect of exercise," J. Appl. Physiol., vol. 98(4) pp. 1154-1162 (2005).
Lamonte, et al., "Physical activity and diabetes prevention," J. Appl. Physiol., vol. 99, pp. 1205-1213 (2005).
Bruunsgaard, "Physical activity and modulation of systemic low-level inflammation," J. Leukoc. Biol., vol. 78(4), pp. 819-835 (2005).
Moldoveanu, et al., "The cytokine response to physical activity and training," Sports Med., vol. 31(2), pp. 115-144 (2001).
Kadowaki, et al., "Adiponectin and adiponectin receptors," Endocr. Rev. vol. 26, pp. 439-451 (2005).
Civitarese, et al., "Role of adiponectin in human skeletal muscle bioenergetics," Cell Metab., vol. 4(1), pp. 75-87 (2006).
Couturier, et al. "Carnitine supplementation to obese Zucker rats prevents obesity-induced type I to type II muscle fiber transition and favors an oxidative phenotype of skeletal muscle," Nutrition & Metabolism, vol. 10(48), pp. 1-11 (2013).
Ingelsson, et al., "Associations of Serum Adiponectin with Skeletal Muscle Morphology and Insulin Sensitivity," J. Clin. Endocrinol. Metab., vol. 94(3), pp. 953-957 (2009).
Shibata, et al. "Adiponectin regulates cutaneous wound healing by promoting keratinocyte proliferation and migration via the ERK signaling pathway," J. Immunol., vol. 189(6), pp. 3231-3241 (2012).
Ezure, et al. "Adiponectin and leptin up-regulate extracellular matrix production by dermal fibroblasts," Biofactors, vol. 31(3-4), pp. 229-236 (2007).
Yamane, et al. "Adiponectin promotes hyaluronan synthesis along with increases in hyaluronan synthase 2 transcripts through an AMP-activated protein kinase/peroxisome proliferator-activated receptor-α-dependent pathway in human dermal fibroblasts," Biochem. and Biophys. Res. Comm. vol. 415, pp. 235-238 (2011).

(Continued)

*Primary Examiner* — Mark V Stevens
(74) *Attorney, Agent, or Firm* — Fay Sharpe LLP

(57) ABSTRACT

A ferment extract of a bacterial strain of the *Bacillus pumilus* species, a method of treatment and/or care of the skin and/or muscles, and cosmetic and/or dermopharmaceutical compositions containing the ferment extract. In particular, the ferment extract is used for muscular endurance, wound healing and skin firmness.

22 Claims, No Drawings

(56) References Cited

OTHER PUBLICATIONS

Wilkinson, et al., "Harry's Cosmeticology," Seventh Edition Longman House, Essex, G.B. pp. 50-73 and 757-799 (1982).
Schaab, et al., "Impregnating Fabrics with Microcapsules," HAPPI pp. 84-86 (May 1986).
Nelson, "Application of microencapsulation in textiles," Int. J. Pharm., 242(1-2), pp. 55-62 (2002).
Elsner, et al., "Antimicrobials and the skin. Physiological and Pathological Flora," in Biofunctional Textiles and the Skin, Curr. Probl. Dermatol. V. 33, pp. 35-41(2006).
Malcolm et al., "Controlled release of a model antibacterial drug from a novel self-lubricating silicone biomaterial," J. Cont. Release, 97(2) pp. 313-320 (2004).
Gottschalck, et al., CTFA International Cosmetic Ingredient Dictionary & Handbook, 12th Edition, pp. 3040-3065 (2008).

* cited by examiner

FERMENT EXTRACT OF A BACTERIAL STRAIN FOR THE INCREASE OF ADIPONECTIN LEVELS

This application claims the benefit of PCT/IB2015/052326, filed Mar. 30, 2015, and EP14382129.6, filed Mar. 31, 2014, from which the PCT application claims priority, the disclosures of which are incorporated herein by reference in their entireties.

FIELD OF THE INVENTION

The disclosed technology relates to a ferment extract of bacterial origin, which increases the adiponectin levels. Said ferment extract is secreted by a strain of the *Bacillus pumilus* species. This invention also relates to the cosmetic or dermopharmaceutical compositions which contain said ferment extract.

BACKGROUND OF THE INVENTION

The skin, mucous membranes, hair and/or nails constitute a physical barrier between the organism and its environment. The skin is composed of two tissues: the epidermis and the dermis. The adipocytes are found in the deeper layer of the dermis, the hypodermis, and they are organized in lobules, separated by septa of connective tissue that contain vessels, nerves and lymph nodes. The main function of adipocytes is the storage of fat as triglycerides in vacuoles.

Adipose tissue plays a crucial role in the regulation of whole-body fatty acid homeostasis. In periods of caloric abundance it stores free fatty acids (FFAs) in the form of triglycerides through their esterification to glycerol and it releases them back into the circulation in times of energy shortage. Adipose tissue also acts as an endocrine organ capable of secreting cytokines, named as adipokines or adipose tissue-derived proteins.

A deposition of adipose tissue in different parts of the body and a decrease in the muscular mass takes place with the age and the lack of adequate physical activity. Regular exercise brings a decrease in fat accumulation and an increase in muscular endurance, which in turn leads to a firmer aspect of some corporal areas and a better physical appearance. Beneficial effects of exercise are thought to be partly mediated by changes in adipokine profile, that is, by increasing the levels of anti-inflammatory cytokines, such as adiponectin [Golbidi S. and Laher I. "*Exercise Induced Adipokine Changes and the Metabolic Syndrome*", *J. Diabetes Res.*, 2014; DOI 2014:726861; Petersen A. M. and Pedersen B. K., "*The anti-inflammatory effect of exercise*", *J. Appl. Physiol.*, 2005, 98(4), 1154-1162; LaMonte M. J. et al., "*Physical activity and diabetes prevention*", *J. Appl. Physiol.*, 2005, 99, 1205-1213; Bruunsgaard H., "*Physical activity and modulation of systemic low-level inflammation*", *J. Leukoc. Biol.*, 2005, 78(4), 819-835]. The effect of the exercise has been described at levels of gene expression, protein ligands, and receptor bindings [Moldoveanu A. I. et al., "*The cytokine response to physical activity and training*", *Sports Med.*, 2001, 31(2), 115-144].

Adiponectin (also known as AdipoQ, ACDC, Acrp30, apM-1, APM1, GBP28, ADPN and ADIPQTL1) is a cytokine secreted by adipose tissue during adipocyte differentiation. Human adiponectin consists of 244 amino acids and has a characteristic domain structure with a collagen-like and a globular C1q-like domain, and it circulates in the blood in at least three homomeric complexes, i.e., trimer, hexamer and higher order multimers. Plasma adiponectin level is inversely correlated with body mass index (BMI) and intra-abdominal fat and furthermore, plasma adiponectin level increases by means of aerobic exercise training [Golbidi S. and Laher I. "*Exercise Induced Adipokine Changes and the Metabolic Syndrome*", *J. Diabetes Res.*, 2014; DOI 2014:726861].

Adiponectin carries out its function through activation of two kinds of receptors, adiponectin receptor 1 (AdipoR1) and adiponectin receptor 2 (AdipoR2). Adiponectin binds to AdipoR1 in skeletal muscle cells, and it activates 5' AMP-activated protein kinase (AMPK) pathways by phosphorylation, initiating a series of molecular responses which finally leads to the stimulation of glucose uptake, fatty acid oxidation, ATP production and mitochondrial biogenesis [Kadowaki T. and Yamauchi T. "*Adiponectin and adiponectin receptors*", *Endocr. Rev.* 2005, 26:439-451; Golbidi S. and Laher I. "*Exercise Induced Adipokine Changes and the Metabolic Syndrome*", *J. Diabetes Res.*, 2014, 2014:726861]. Furthermore, the treatment of human myotubes with adiponectin has been disclosed to induce mitochondrial biogenesis, palmitate oxidation and citrate synthase activity [Civitarese A. E. et al., "*Role of adiponectin in human skeletal muscle bioenergetics.*" *Cell Metab.*, 2006, 4(1):75-87], therefore, inducing an increase of the strength and tone of the muscle fibers similar to the one achieved by physical exercise.

Skeletal muscles are composed of myocytes that form muscle fibers (myofibers). The myofibers are formed from the fusion of development myoblasts (a type of embryonic progenitor cell) in a process known as myogenesis. There are two major types of muscle fibers which differ in their Myosin heavy chain (MyHC) isoforms and their enzymatic capacity. Muscles are composed by a mixture of different types of muscle fibers. Type I fibers (slow twitch) have aerobic activity, high oxidative capacity due to high mitochondria content (express enzymes that oxidize fatty acids), are myoglobin-rich with red appearance and express the protein marker Myosin heavy chain 7 (MyH7), which is specific for Type I fibers [Couturier A. et al. "*Carnitine supplementation to obese Zucker rats prevents obesity-induced type II to type I muscle fiber transition and favors an oxidative phenotype of skeletal muscle*" *Nutrition & Metabolism*, 2013, 10:48]. Type II fibers (fast twitch) have anaerobic activity, low oxidative capacity due to low mitochondria content and depend on glycolytic metabolism to generate ATP (adenosine triphosphate). The proportion of Type I and Type II fibers depends on the action of the muscle: Type I fibers are mainly involved in aerobic exercise, in comparison with Type II fibers, which are mainly involved in anaerobic exercise, i.e. the higher the number of Type I fibers, the higher the muscular endurance. Individuals with high skeletal muscle capillary density and individuals with high proportion of Type I fibers show high concentrations of circulating adiponectin [Ingelsson E. et al., "*Associations of Serum Adiponectin with Skeletal Muscle Morphology and Insulin Sensitivity*", *J Clin Endocrinol Metab*, 2009, 94(3):953-957]. Therefore, an increase in the level of circulating adiponectin is expected to increase the proportion of Type I fibers and the muscular endurance.

Furthermore, adiponectin has been reported to induce or accelerate the healing process of skin wounds [EP1651161 B1] by promoting keratinocyte proliferation and migration [Shibata S. et al. "*Adiponectin regulates cutaneous wound healing by promoting keratinocyte proliferation and migration via the ERK signaling pathway*", *J. Immunol.*, 2012, 189(6):3231-41]. Adiponectin has been also reported to increase the collagen synthesis and to upregulate Hyaluronic acid synthase 2 gene expression, which increases the synthesis of hyaluronic acid [Ezure T. et al. "*Adiponectin and leptin up-regulate extracellular matrix production by dermal fibroblasts*", Biofactors. 2007, 31(3-4):229-36; Yamane T. et al. "*Adiponectin promotes hyaluronan synthesis along with increases in hyaluronan synthase 2 transcripts through an AMP-activated protein kinase/peroxisome proliferator-activated receptor-α-dependent pathway in human dermal fibroblasts*", Biochem. and Biophys. Res. Comm. 2011, 415, 235-238].

Surprisingly the inventors of the present invention have found that the ferment extract from a strain of the *Bacillus pumilus* species increases the adiponectin levels, mitochondrial activity in muscle, ATP levels in muscle and muscular endurance.

SUMMARY OF THE INVENTION

The disclosed technology provides a solution for the increase of the level of adiponectin in adipocytes, and mitochondrial activity in muscle by a ferment extract of a strain of *Bacillus pumilus* species.

In accordance with one aspect, a method for increase of the level of adiponectin, increase of mitochondrial activity in muscle, increase of muscular endurance, stimulation of wound healing and/or reepithelialization of the skin uses a ferment extract of a strain of *Bacillus pumilus* species.

In accordance with another aspect, a cosmetic or dermopharmaceutical composition includes a cosmetically or pharmaceutically effective quantity of the ferment extract of a strain of *Bacillus pumilus* species and at least one cosmetically and/or dermopharmaceutically acceptable excipient and/or ingredient.

In accordance with another aspect, a method of increasing the adiponectin levels, increasing the mitochondrial activity in muscle, increasing muscular endurance, stimulating wound healing and/or reepithelialization of the skin, stimulating collagen synthesis and/or hyaluronic acid synthesis, treatment of skin aging, treatment of skin wrinkles, treatment of skin firming includes administering a cosmetically or pharmaceutically effective amount of the ferment extract of a strain of *Bacillus pumilus* species.

DESCRIPTION OF THE INVENTION

This invention relates to the ferment extract of a strain of *Bacillus pumilus* species, to the ferment extract for its use to increase the adiponectin levels and cosmetic or dermopharmaceutical compositions which comprise the ferment extract. Surprisingly the inventors of this invention have also found that the aforementioned ferment extract increases the mitochondrial activity in muscle, muscular endurance.

Definitions

In order to facilitate the comprehension of this invention, the meanings of some terms and expressions as used in the context of the invention are included.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

The term "treatment", as used in the context of this specification when it is not accompanied by the qualifications "cosmetic, non-therapeutic", means the administration of a compound according to the invention to alleviate or eliminate a disease or disorder or reduce or eliminate one or more symptoms associated with this disease or disorder. The term "treatment" also covers the ability to alleviate or eliminate the physiological consequences of the disease or disorder.

When the term "treatment" is accompanied by the qualifications "cosmetic, non-therapeutic" they refer to the application of the compound to the skin with the aim of improving the cosmetic qualities of the skin such as and not restricted to, their level of hydration, elasticity, firmness, shine, tone or texture, among others. The term "care" in this invention refers to the maintenance of the qualities of the skin and it includes the body and/or hair hygiene. These qualities are subject to improvement and maintained through a cosmetic treatment and/or care of the skin both in healthy subjects as well as those which present diseases and/or disorders of the skin, such as and not restricted to, ulcers and lesions on the skin, psoriasis, dermatitis, acne or rosacea, among others.

The term "prevention", as used in this invention, refers to the ability of a compound of the invention to prevent, delay or hinder the appearance or development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, among others.

Therefore, a first aspect of the present invention relates to the ferment extract of a strain of *Bacillus pumilus* species for its use in the increase of the level of adiponectin, increase of mitochondrial activity in muscle, increase of muscular endurance, stimulation of wound healing and/or reepithelialization of the skin. In one embodiment, the increase of mitochondrial activity in muscle is an increase of the level of ATP and/or citrate synthase activity in muscle. In other embodiment, the level of adiponectin is the level of circulating adiponectin. In other embodiments, the increase of muscular endurance is an increase of the aerobic endurance. In another embodiment, the increase of the aerobic endurance is an increase in the proportion of Type I fibers in muscle.

In another aspect, the present invention relates to the use of the ferment extract of a strain of *Bacillus pumilus* species for the cosmetic, non-therapeutic increase of the adiponectin level in adipocytes, cosmetic, non-therapeutic stimulation of collagen synthesis and/or hyaluronic acid synthesis in the skin, cosmetic, non-therapeutic treatment and/or prevention of skin aging, cosmetic, non-therapeutic treatment and/or prevention of skin wrinkles, cosmetic, non-therapeutic treatment of skin firming and/or for the cosmetic, non-therapeutic prevention of loss of skin firmness.

In one embodiment, the treatment of the skin is carried out by topical or transdermal application.

In other embodiment, the increase of mitochondrial activity in muscle, increase of muscular endurance, stimulation of wound healing and/or reepithelialization of the skin are consequence of the increase of the adiponectin level.

In another embodiment, the strain of Bacillus pumilus species is a strain of Bacillus pumilus species with deposit number LMG P-28202. Said strain has been deposited on Mar. 11, 2014 at the Belgian Coordinated Collection of Microorganisms (BCCM)/Laboratorium voor Microbiologie-Bacteriëverzameling (LMG) (BCCM/LMG) (University Ghent, K. L. Ledeganckstraat 35, B-9000 Ghent, Belgium) as institution legally recognized for said purpose according to the Budapest Treaty on the International Recognition of the Deposit of Microorganisms on Apr. 28, 1977.

In other embodiment, the ferment extract of the strain of Bacillus pumilus species contains peptidic and glucidic material having a molecular weight less than 7000 Da, or less than 5000 Da. In another embodiment, the ferment extract of the strain of Bacillus pumilus species does not contain secondary amines. In another embodiment, the ferment extract of the strain of Bacillus pumilus species does not contain phenolic compounds.

In another embodiment, the ferment extract of the strain of Bacillus pumilus species has a residence time between 9 and 20 minutes, between 10 and minutes at a chromatographic analysis High Performance Liquid Chromatography (HPLC), with a chromatographic column TSKGel G2000SWXL, 5 m, 125 Å 7.8 mm×30 mm (TOSOH Bioscience) and water with 0.1M pH=6.70+0.1M phosphate buffer+0.1M sodium sulfate as eluent.

In another embodiment, the extract is obtained through fermentation of the strain of Bacillus pumilus species in a suitable culture medium, conventionally stirred and aerated for synthesizing and secreting said product to the culture medium followed by subsequent purification. Fermentation to produce the extract of this invention can be carried out in a medium stirred and aerated at a temperature between 10° C. and 40° C., or between 20° C. and 35° C., the medium having a pH between 6.5 and 9, or around 7.0, adjusting it if necessary during fermentation. The duration of the fermentation is between 12 to 120 hours, or between 24 and 72 hours.

The culture medium in the fermentation of the strain of Bacillus pumilus species comprises nitrogen and/or carbon sources such as yeasts extracts, malt extracts and/or peptones, with concentrations of each one of these components of 0.1 to 20 g/L, or of 0.5 to 10 g/L. The culture medium in the fermentation of the strain of Bacillus pumilus species also contains sea salts at a concentration between 5 and 40 g/L, or between 25 and 35 g/L.

In another embodiment, the culture medium in the fermentation of the strain of Bacillus pumilus species comprises exogenous sugars, such as and not restricted to, galactose, glucose, mannose, amygdalin, cellobiose, maltose, starch, glycogen, lactose, mixtures thereof and/or extracts containing mixtures of these sugars can be used as additional carbon source in the fermentation culture medium. In one embodiment, an exogenous supply of glucose of 0.5 to 40 g/L, or from 5 to 25 g/L is provided to the fermentation culture medium. In other embodiment, the fermentation culture medium is free of additional nitrogen or carbon sources.

In another embodiment, in addition to sea salts, additional mineral salts are also provided to the fermentation culture medium of the strain of Bacillus pumilus species. These salts are chosen from among salts which provide the ions $Na^+$, $K^+$, $NH_4^+$, $Ca^{2+}$, $Mg^{2+}$, $PO_4^{3-}$, $SO_4^{2-}$, $Cl^-$, $F^-$, $I^-$, $CO_3^{2-}$, $NO_3^-$, citrates, or trace elements such as Cu, Mn, Mo, Fe, Sr, B, Br, Si, Al, Li, and Zn.

In other embodiment, the method of isolation and purification of the ferment extract is carried out by the methods known by the person skilled in the art such as, centrifugation and filtration. In one embodiment, centrifugation and filtration steps are directed to separate the strain of the Bacillus pumilus species from the supernatant where the ferment extract is found. In one embodiment, the strain of Bacillus pumilus species is a strain of Bacillus pumilus species with deposit number LMG P-28202.

Another aspect of this invention relates to a cosmetic or dermopharmaceutical composition characterized in that it comprises a cosmetically or dermopharmaceutically effective quantity of the ferment extract of the strain of Bacillus pumilus species and at least one cosmetically and/or dermopharmaceutically acceptable excipient and/or ingredient. In one embodiment, the strain of Bacillus pumilus species is a strain of Bacillus pumilus species with deposit number LMG P-28202. Said compositions are prepared by the conventional methods known by the persons skilled in the art ["Harry's Cosmeticology", Seventh edition, (1982), Wilkinson J. B., Moore R. J., ed. Longman House, Essex, GB].

The cosmetically or dermopharmaceutically effective quantity of the ferment extract of the strain of Bacillus pumilus species in the composition of the invention to be administered, as well as its dosage, will depend on numerous factors, including age, condition of the patient, the nature or severity of the condition or disorder to be treated and/or cared for, the route and frequency of administration and the nature of the ferment extract to be used.

"Cosmetically or dermopharmaceutically effective quantity" is understood to be a non-toxic but sufficient quantity of an ingredient to provide the desired effect. For example, the ferment extract of the strain of Bacillus pumilus species is used at cosmetic or dermopharmaceutic concentrations to achieve the desired effect; i.e. with regard to the total weight of the composition, between 0.0000000001% (in weight) and 20% (in weight); between 0.00000001% (in weight) and 10% (in weight), between 0.000001% (in weight) and 5% (in weight) or between 0.0001% (in weight) and 5% (in weight).

In one embodiment, the ferment extract of the invention can also be incorporated into cosmetic or dermopharmaceutical delivery systems and/or sustained release systems.

The term "delivery systems" relates to a diluent, adjuvant, excipient, vehicle or additive with which the ferment extract of the invention is administered. These cosmetic or dermopharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time. In one embodiment, the gradual release provides a relatively constant compound release level over a period of time.

Examples of delivery or sustained release systems include, without limiting sense, liposomes, mixed liposomes, oleosomes, niosomes, ethosomes, milliparticles, microparticles, nanoparticles and solid lipid nanoparticles, nanostructured lipid supports, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as microemulsions and nanoemulsions, which can be added to achieve a greater penetration of the ferment extract of the invention. In one embodiment, the delivery or sustained release systems are liposomes, surfactant-phospholipid mixed micelles, microemulsions, water-in-oil microemulsions with an internal reverse micelle structure and nanocapsules containing microemulsions. In one embodiment, the delivery or sustained release systems are liposomes, microemulsions, or liposomes containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part. In one embodiment, the release provides a relatively constant compound release level over a period of time. The amount of ferment extract contained in the sustained release system will depend, for example, on where the composition is to be administered, the kinetics and duration of the release of the ferment extract of the invention, as well as the nature of the condition and/or disorder to be treated and/or cared for.

In one embodiment, the composition containing the ferment extract of this invention is adsorbed on solid organic polymers or solid mineral supports, such as and not restricted to, talc, bentonite, silica, starch or maltodextrin among others.

In one embodiment, the composition containing the ferment extract of the strain of *Bacillus pumilus* species is incorporated into fabrics, non-woven fabrics or medical devices which are in direct contact with the skin, thus releasing the ferment extract of the invention whether by biodegradation of the binding system to the fabric, non-woven fabric or medical device, or due to the friction between them and the body, due to body moisture, the skin's pH or body temperature. In other embodiment, the ferment extract of the invention is incorporated into fabrics and non-woven fabrics used in the manufacture of garments that are in direct contact with the body. In one embodiment, the fabrics, non-woven fabrics and medical devices containing the ferment extract of the invention are used for the treatment and/or care of conditions and/or disorders which improve or are prevented by the increase of adiponectin levels, increase of the mitochondrial activity, stimulation of wound healing and/or reepithelialization of the skin, or by stimulation of collagen synthesis.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) *HAPPI May* 1986; Nelson G., "*Application of microencapsulation in textiles*", (2002), *Int. J. Pharm.,* 242(1-2), 55-62; *"Biofunctional Textiles and the Skin*" (2006) *Curr. Probl. Dermatol.* v.33, Hipler U. C. and Elsner P. eds. S. Karger A G, Basel, Switzerland; Malcolm R. K. et aL, "*Controlled release of a model antibacterial drug from a novel self-lubricating silicone biomaterial*", (2004), *J. Cont. Release,* 97(2), 313-320]. In one embodiment, the fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or dermopharmaceutical compositions containing the ferment extract of this invention can be used in different types of compositions of topical or transdermal application, optionally including cosmetically and/or dermopharmaceutically acceptable excipients necessary for formulating the desired administration form.

In one embodiment, the compositions of topical or transdermal application are produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, liquid crystals, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. In other embodiment, these topical or transdermal application formulations are incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they are incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

In other embodiment, the cosmetic or dermopharmaceutical composition of the invention includes agents which increase the percutaneous absorption of the ferment extract of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. In other embodiment, the cosmetic or dermopharmaceutical composition of this invention is applied into local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the ferment extract of the invention. The application area will be determined by the nature of the condition and/or disorder to be treated and/or cared for.

Among the cosmetically or dermopharmaceutically acceptable excipients and/or ingredients contained in the cosmetic or dermopharmaceutical compositions described in this invention are additional ingredients commonly used in cosmetic or dermopharmaceutical compositions such as and not restricted to, other agents which increase the level of adiponectin in adipocytes, other agents which increase the mitochondrial activity, other agents which increase the ATP level in muscle, other agents stimulating healing, other coadjuvant healing agents, other agents stimulating reepithelialization, other coadjuvant reepithelialization agents, agents which reduce the triglyceride content of adipocytes, agents delaying adipocyte differentiation, agents that reduces the amount of nocturnin, agents inhibiting the nocturnin expression, lipolytic agents or agents stimulating lipolysis, venotonic agents, agents modulating PGC-1α expression, agents inhibiting the activity of PPARγ, anti-cellulite agents, agents which diminish the sebum production, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor clustering, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, antiglycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of components of the stratum corneum, ceramides, fatty acids, agents that inhibit collagen degradation, agents that inhibit matrix metalloproteinases, agents that inhibit elastin degradation, agents that inhibit serine proteases such as kallikreins, leukocyte elastase or cathepsin G, agents stimulating fibroblast proliferation, agents stimulating keratinocyte proliferation, agents stimulating melanocyte proliferation, agents stimulating keratinocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, astringent agents, agents which inhibit the activity of PAR-2, cytokines, growth factors, agents acting on capillary circulation and/or microcirculation, agents stimulating angiogenesis, agents that inhibit vascular permeability, agents acting on cell metabolism, agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and with the ferment extract produced by a strain of *Bacillus pumilus* species. Likewise, the nature of these additional ingredients should not unacceptably alter the benefits of the ferment extract of this invention. The nature of these additional ingredients can be synthetic or natural, such as plant extracts, or come from a biotechnological procedure, or from a combination of a synthetic procedure and a biotechnological procedure. Additional examples can be found in *CTFA International Cosmetic Ingredient Dictionary & Handbook, 12th Edition* (2008). In the context of this invention, biotechnological procedure is understood to be any procedure to produce the active ingredient, or part of it, in an organism, or in part of it.

In one embodiment, the agent that reduces the triglyceride content of adipocytes, agent that delays adipocyte differentiation, anti-cellulite agent, lipolytic agent, venotonic agent, agent inhibiting PGC-1α expression or agent inhibiting the activity of PPARγ is chosen, for example and not restricted to extracts or hydrolyzed extracts of *Alchemilla vulgaris, Angelica sinensis, Armeniacae* sp., *Arnica montana* L, *Atractylodis platycodon,* bamboo, *Betula alba, Bupleurum chinensis, Calendula officinalis,* cangzhu, *Cecropia obtusifolia, Celosia cristata, Centella asiatica, Chenopodium quinoa, Chrysanthellum indicum, Cimifuga racemosa, Citrus aurantium amara, Cnicus benedictus, Coffea arabica, Cola nitida, Coleus barbatus, Coleus blumei, Coleus esquirolii, Coleus forskohlii, Coleus scutellarioides, Coleus* sp., *Coleus xanthantus, Commiphora myrrha, Crithmum maritimum, Cuminum cyminum, Dioscorea collettii, Dioscorea villosa, Eugenia caryophyllus, Filipendula ulmaria* L, *Foeniculum vulgare, Fucus vesiculosus, Gelidium Cartilagineum, Ginkgo biloba,* ginkgo biloba, *Glycine max, Glycyrrhiza glabra, Hedera helix* (ivy extract), *Hibiscus sabdariffa, Hordeum vulgare, Humulus lupulus, Hypericum perforaturn, Ilex paraguariensis, Kigelia africana, Laminaria digitata, Lupinus perennis, Nelumbium speciosum, Orthosiphon stamineus* benth, *Panax ginseng, Paullinia cupana, Peumus boldus, Phyllacantha fibrosa, Piper methysticum, Piper nigrum, Prunella vulgaris, Prunus amygdalus dulcis, Rosmarinus officinalis, Rubus idaeus, Ruscus aculeatus* (extract of Butcher's broom), *Salvia officinalis* L, *Sambucus nigra, Serenoa repens, Smilax aristolochiaefolia, Spirulina platensis* algae, *Taraxacum erythrospermum, Taraxacum officinale,* green tea, *Ulmus rubra, Uncaria tomentosa, Verbena officinalis, Vitex agnus-castus, Dysmorphococcus globosus,* among others, alverin, alverin citrate, dihydromyricetin, coenzyme A, lipase, cerulenin, rutin, glaucine, esculin, visnadine, caffeine, theophylline, theobromine, aminophylline, xanthine, carnitine, forskolin, escin, ruscogenin, hederin, triethanolamine iodide, AMPc synthesis inducing agents, Lanachrys® [INCI: *Chrysanthellum Indicum* Extract] marketed by Atrium/Unipex, Slim-Excess™ [INCI: Water, Butylene Glycol, Sodium Chloride, Hydrolyzed Carrageenan, Xanthan Gum], Sveltine™ [INCI: Water, Butylene Glycol, Carnitine, Lecithin, Caffeine, Carbomer, Salicylic Acid, Atelocollagen, *Centella Asiatica* Extract, Esculin, Sodium Chondroitin Sulfate], Peru Liana [INCI: Uncaria *Tomentosa* Extract] or Flavenger™ [INCI: Caprylic/Capric Triglyceride, Silica Dimethyl Silylate, Glyceryl Oleate, Quercetin Caprylate] marketed by BASF, Scopariane [INCI: Sphacelaria Scoparia], Phyco® R75 [INCI: *Laminaria Digitata*], Pheoslim™ [INCI: *Phyllacantha Fibrosa* Extract], Buckwheat Wax [INCI: *Polygonum fagopyrum*] or Areaumat™ Samphira [INCI: *Crithmum Maritimum* Extract], Actiporine 8.G™ [Glycerine, Aqua, *Jania rubens* extract] marketed by Codif, Slimming Factor Karkade™ [INCI: *Hibiscus Sabdariffa*] marketed by Cosmetochem, Liposuctionine™ [proposed INCI: Acetyl Hexapeptide] marketed by Infinitec Activos, Xantalgosil ©® [INCI: Acefylline Methylsilanol Mannuronate], Theophyllisilane ©® [INCI: Methylsilanol Carboxymethyl Theophylline Alginate], Glutrapeptide® [INCI: Pyroglutamylamidoethyl Indole] or Cafeisilane ©® [INCI: Siloxanetriol Alginate, Caffeine, Butylene Glycol] marketed by Exsymol, Timiline® [INCI: Polyglucuronic acid] marketed by Greentech, Visnadine [INCI: Visnadine] or *Ginkgo Biloba* Dimeric Flavonoids Phytosome [INCI: Phospholipids, *Ginkgo Biloba* Leaf Extract] marketed by Indena, Slimfit® LS 9509 [INCI: Cecropia *Obtusifolia* Bark Extract] marketed by Laboratoires Serobiologiques/Cognis/BASF, Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Liporeductyl® [INCI: Water, Glycerin, Lecithin, Caffeine, Butcher broom (*Ruscus Aculeatus*) Root Extract, Maltodextrin, Silica, Tea-Hydroiodide, Propylene Glycol, Ivy (*Hedera Helix*) Extract, Carnitine, Escin, Tripeptide-1, Xanthan Gum, Carrageenan (*Chondrus Crispus*), Disodium EDTA] marketed by Lipotec/Lubrizol, Iso-Slim Complex™ [INCI: Soy Isoflavones, Caffeine, Carnitine, *Spirulina Platensis* Extract, Polysorbate 80, Alcohol, Phenoxyethanol, Aqua], Happybelle-PE™ [INCI: Lecithin, *Vitex Agnus Castus* Extract, Glycerin, Ascorbyl Tetraisopalmitate, Tocopherol, Caprylic/Capric Triglyceride, Cyclodextrin, Alcohol, Water] or AmaraShape® [INCI: Lecithin, Caffeine, *Citrus Aurantium Amara* Extract, Pentylene Glycol, Alcohol, Water] marketed by Mibelle Biochemistry, Regu®-Slim [INCI: Maltodextrin, Caffeine, *Paullinia Cupana* Seed Extract, Carnitine, Microcrystalline Cellulose, Cysteic Acid, Pantheine Sulfonate] or Regu®-Shape [INCI: Isomerized Linoleic Acid, Lecithin, Glycerin, Polysorbate 80] marketed by Pentapharm/DSM, Provislim™ [INCI: Propanediol, Water (Aqua), Fisetin, Raspberry Ketone], Myriceline™ [INCI: Dihydromyricetin] or Drenalip™ [INCI: Ruscus *Aculeatus* Root Extract, *Citrus Medica* Limonum Peel Extract, Solidago Virgaurea Extract, *Astragalus Membranaceus* Root Extract] marketed by Provital, Actisculpt® [INCI: *Commiphora* Myrrha Extract, *Coleus Forskohlii* Root Extract] marketed by Givaudan, Perfeline® [INCI: Water, Carnitine, Caffeine, Ruscus *Aculeatus* Extract] or CellActive® Shape [INCI: *Chlorella Vulgaris*/*Lupinus Albus* Protein Ferment, *Coleus Forskohlii*, Caffeine] marketed by Rahn, ProContour™ [INCI: Water, Alcohol, Lecithin, Caffeine, Carnitine, *Centella Asiatica* Leaf Extract, Potassium Phosphate, *Coleus Forskohlii* Root Extract] marketed by Rovi Cosmetics, Unislim™ [INCI: *Ilex Paraguariensis* (Leaf) Extract, Water, Butylene Glycol, *Coffea Arabica* (Coffee) Seed Extract (Bean), PEG-60 Almond Glycerides, Glycerin, Cetyl Hydroxyethylcellulose], Redulite™ [INCI: Glycerin, Aqua, Ethoxydiglycol, *Sambucus Nigra*, Sodium Polyacrylate], Pleurimincyl™ [INCI: Caffeine, *Bupleurum Chinensis* extract], Phytotal™ SL [INCI: Glycerin, *Verbena Officinalis* Extract, Butylene Glycol, *Sambucus Nigra* Flower Extract, *Eugenia Caryophyllus* (Clove) Flower Extract, Lecithin], Phytosonic™ [INCI: Aqua, *Euglena Gracilis* Extract, Caffeine, Glaucium Flavum Leaf Extract], Ovaliss™ [INCI: Glycerin, Aqua, Coco-glucoside, Caprylyl Glycol, Alcohol, Glaucine], Lipocare™ [INCI: Caffeine, Coenzym A, *Bupleurum Chinensis* extract], Cyclolipase™ [INCI: Glyceryl Polymethacrylate, Water, Caffeine, Lipase, Adenosine Phosphate], Coaxel™ [INCI: Caffeine, Coenzyme A, Carnitine, Water, Glycerin], Bodyfit™ [INCI: Glycerin, Aqua (Water), Coco-Glucoside, Caprylyl Glycol, Alcohol, Glaucine] or Vexel™ [INCI: Aqua, Propylene glycol, Lecithin, Caffeine, Palmitoyl carnitine] marketed by Sederma/Croda, Voluform™ [INCI: Palmitoyl isoleucine], Adipoless™ [INCI: Butylene Glycol, *Chenopodium Quinoa* Seed Extract] marketed by Seppic, Slimactive® [INCI: *Peumus Boldus* Leaf Extract], Remoduline® [INCI: *Citrus Aurantium Amara* Flower Extract], Pro-Sveltyl® [INCI: Nelumbium *Speciosum* Extract], Biosculptine® [INCI: Hydrolyzed *Celosia Cristata* Flower/Seed Extract, Hydrolyzed *Prunella Vulgaris* Extract], Affiness® [INCI: Hydrolyzed *Coriandrum Sativum* Fruit Extract, *Citrus Aurantium Dulcis* (Orange) Fruit Extract] or Stemsvelt® [INCI: Water, Butylene Glycol, *Silybum marinum* extract] marketed by Silab, Delipidol [INCI: Tyrosyl Punicate], Guaraslim® [INCI: Butylene Glycol, Water, Caffeine, *Paullinia Cupana* Seed Extract, *Ptychopetalum Olacoides* Bark Extract] or Caobromine® [INCI: *Theobroma* Cocoa Shell Extract] marketed by Solabia, Abdoliance™ [INCI: Sucrose palmitate, Polysorbate 20, Glyceryl Linolenate, *Paullinia Cupana* Seed Extract, Maltodextrin, *Prunus* Amygdalus *Dulcis* (Sweet Almond) Oil, Lecithin, Water, *Citrus Aurantium Amara* (Bitter Orange) Peel Extract, Phenoxyethanol, Tocopherol], Betaphroline [INCI: Tephrosia *Purpurea* Seed Extract] or PRO-DG™ [INCI: Water, Plankton extract] marketed by Soliance, UCPeptide™ V [INCI: Water, Butylene Glycol, Pentapeptide] or ATPeptide™ IS [INCI: Tripeptide-3] marketed by Vincience/ISP among others, or mixtures thereof.

In one embodiment, the firming and/or redensifying and/or restructuring agent is chosen, for example and not restricted to, from the group formed by extracts of *Malpighia punicifolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: *Triticum Vulgare, Silybum Marianum*, Glycine Soy, *Equisetum Arvense, Alchemilla Vulgari, Medicago Sativa, Raphanus Sativus*] or Polyplant® Refirming [INCI: Coneflower, Asiatic Centella, Fucus, Fenugreek] marketed by Provital, Lanablue® [INCI: Sorbitol, Algae Extract] marketed by Atrium Biotechnologies/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/ Croda, Dermosaccharides® HC [INCI: Glycerin, Water (Aqua), Glycosaminoglycans, Glycogen], Aglycal® [INCI: Mannitol, Cyclodextrin, Glycogen, Arctostaphylos Uva *Ursi* Leaf Extract], Cytokinol® LS [INCI: Hydrolyzed Casein, Hydrolyzed Yeast Protein, Lysine HCl] or Firmiderm® LS9120 [INCI: Terminalia Catappa Leaf Extract, *Sambucus Negra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Uplevity™ [INCI: Acetyl Tetrapeptide-2] or Adifyline® [INCI: Acetyl Hexapeptide-38] marketed by Lipotec/Lubrizol, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/ Engelhard/BASF, Syn®-Coll [INCI: Palmitoyl Tripeptide-5] marketed by Pentapharm/DSM, Hydriame® [INCI: Water (Aqua), Glycosaminoglycans, *Sclerotium* Gum] marketed by Atrium Biotechnologies/Unipex Innovations or IP2000™ [INCI: Dextran, Trifluoroacetyl Tripeptide-2] marketed by Institut Europeen de Biologie Cellulaire/Unipex Innovations, among others.

In one embodiment, the agent stimulating the synthesis of dermal or epidermal macromolecules is chosen, for example and not restricted to, from the group formed by collagen synthesis-stimulating agents, elastin synthesis-stimulating agents, decorin synthesis-stimulating agents, laminin synthesis-stimulating agents, chaperone synthesis-stimulating agents, sirtuin synthesis-stimulating agents, sirtuin activating agents, aquaporin synthesis-modulating agents, fibronectin synthesis-stimulating agent, agents that inhibit collagen degradation, agents that inhibit elastin degradation, agents that inhibit serine proteases such as kallikreins, leukocyte elastase or cathepsin G, agents stimulating fibroblast proliferation, and DNA repairing agents and/or DNA protecting agents, such as and not restricted to extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of zooplankton *Salina*, the fermentation product of milk with *Lactobacillus Bulgaricus*, asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: *Pseudoalteromonas* Ferment Extract], Decorinyl® [INCI: Tripeptide-10 Citrulline], Serilesine® [INCI: Hexapeptide-10], Lipeptide [INCI: Hydrolyzed Vegetable Protein], Aldenine® [INCI: Hydrolyzed Wheat Protein, Hydrolyzed Soy Protein, Tripeptide-1], Relistase™ [INCI: Acetylarginyltriptophyl Diphenylglycine], Thermostressine™ [INCI: Acetyl Tetrapeptide-22], Peptide AC29 [INCI: Acetyl Tripeptide-30 Citrulline], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Uplevity™ [INCI: Acetyl Tetrapeptide-2] or Adifyline™ [INCI: Acetyl Hexapeptide-38] marketed by Lipotec/Lubrizol, Drieline® PF [INCI: Yeast Betaglucan] marketed by Alban Muller, Phytovityl C® [INCI: Aqua, *Zea Mays* Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, minerals such as calcium, among others, retinoids and their derivatives, isoflavonoids, carotenoids, in particular lycopene, pseudodipeptides, retinoids and their derivatives such as retinol or retinyl palmitate, among others, or heparinoids, among others.

In one embodiment, the anti-wrinkle and/or antiaging agent is chosen, for example and not restricted to, from the group formed by the extracts or hydrolyzed extracts of *Vitis vinifera, Rosa canina, Curcuma longa, Theobroma cacao, Ginkgo biloba, Leontopodium alpinum* or *Dunaliella salina* among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage [INCI: teprenone], Resistem™ [INCI: *Globularia Cordifolia* Ferment] or Dermaxyl® [INCI: Palmitoyl Oligopeptide] marketed by Sederma/Croda, Vialox® [INCI: Pentapeptide-3], Syn® Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum] or Preregen® [INCI: *Glycine soja* (Soybean) Protein, Oxido Reductases] marketed by Pentapharm/DSM, Myoxinol™ [INCI: Hydrolyzed Hibiscus *esculentus* Extract], Syniorage™ [INCI: Acetyl Tetrapeptide-11], Dermican™ [INCI: Acetyl Tetrapeptide-9] or DN AGE™ LS [INCI: *Cassia alata* leaf Extract] marketed by Laboratoires Serobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolyzed Wheat Protein, Hydrolyzed Soy Protein, Tripeptide-1], Preventhelia™ [INCI: Diaminopropionoyl Tripeptide-33], Decorinyl® [INCI: Tripeptide-10 Citrulline], Decorinol® [INCI: Tripeptide-9 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Thermostressine® [INCI: Acetyl Tetrapeptide-22], Lipochroman™ [INCI: Dimethylmethoxy Chromanol], Chromabright™ [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide-10 Citrulline], Hyadisine™ [INCI: *Pseudoalteromonas* Ferment Extract], Hyanify™ [INCI: Saccharide Isomerate], Diffuporine™[INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Adifyline™[INCI: Acetyl Hexapeptide-38], Uplevity™ [INCI: Acetyl Tetrapeptide-2] or Juvefoxo™ [INCI: Acetyl Hexapeptide-51 amide] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract] or Quintescine™ IS [INCI: Dipeptide-4] marketed by Vincience/ISP/Ashland, BONT-L-Peptide™ [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen®4 [INCI: Acetyl Tetrapeptide-2] marketed by Atrium/Unipex Innovations, EquiStat™ [INCI: *Pyrus malus* Fruit Extract, *Glycine soja* Seed Extract] or Juvenesce™ [INCI: Ethoxydiglicol and Caprylic Triglyceride, Retinol, Ursolic Acid, Phytonadione, Ilomastat] marketed by Coletica/Engelhard/BASF, Ameliox™ [INCI: Carnosine, Tocopherol, *Silybum marianum* Fruit Extract] or PhytoCellTec™ *Malus Domestica* [INCI: *Malus domestica* Fruit Cell Culture] marketed by Mibelle Biochemistry, Bioxilift® [INCI: *Pimpinella anisum* Extract] or SMS Anti-Wrinkle® [INCI: *Annona squamosa* Seed Extract] marketed by Silab, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

In one embodiment, the agent stimulating healing, coadjuvant healing agent, agent stimulating reepithelialization, coadjuvant reepithelialization agent, is chosen, for example and not restricted to, from the group formed by extracts or hydrolyzed extracts of *Aristolochia clematis, Centella asiatica, Rosa moschata, Echinacea angustifolia, Symphytum officinal, Equisetum arvense, Hypericum perforaturn, Mimosa tenuiflora, Persea gratisima, Prunus africanum, Tormentilla erecta, Aloe vera*, Polyplant® Epithelizing [INCI: *Calendula* off icinalis, *Hypericum perforatum, Chamomilla recutita, Rosmarinus officinalis*] marketed by Provital, Cytokinol® LS 9028 [INCI: Hydrolyzed Casein, Hydrolyzed Yeast Protein, Lysine HCl] marketed by Laboratories Sérobiologiques/Cognis or Deliner® [INCI: *Zea mays* (Corn) Kernel Extract] marketed by Coletica/Engelhard, allantoin, cadherins, integrins, selectins, hyaluronic acid receptors, immunoglobulins, fibroblast growth factors, connective tissue growth factors, platelet-derived growth factors, vascular endothelial growth factors, epidermal growth factors, insulin-like growth factors, keratinocyte growth factor, colony-stimulating factor, transforming growth factor beta, tumor necrosis factor-alpha, interferons, interleukins, matrix metalloproteinases, protein tyrosine phosphatase receptors, Antarcticine® [INCI: *Pseudoalteromonas* Ferment Extract], Bodyfensine® [INCI: Acetyl Dipeptide-3 Aminohexanoate] or Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide 10 Citrulline, Tripeptide-1], Xpertmoist™ [INCI: Glycerin, *Pseudoalteromonas* Ferment Extract, Xanthan Gum, Proline, Alanine, Serine, Ethylhexylglycerin, Caprylyl Glycol], Serilesine® [INCI: Hexapeptide-10], Delisens™ [INCI: Acetyl Hexapeptide-49] or Thermostressine™ [INCI: Acetyl Tetrapeptide-22], marketed by Lipotec/Lubrizol, among others, and/or mixtures thereof.

Applications

Other aspects of this invention refers to the use of the ferment extract of a strain of *Bacillus pumilus* species in the preparation of cosmetic or dermopharmaceutical compositions for increasing the adiponectin levels, increasing the mitochondrial activity in muscle, increasing muscular endurance, stimulating wound healing and/or reepithelialization of the skin, stimulating collagen synthesis and/or hyaluronic acid synthesis, treatment and/or prevention of skin aging, treatment and/or prevention of skin wrinkles, treatment of skin firming and/or prevention of loss of skin firmness. In one embodiment, the adiponectin level is the level of circulating adiponectin. In another embodiment, the adiponectin level is adiponectin level in adipocytes. In one embodiment, the increase of mitochondrial activity in muscle is an increase of the level of ATP and/or citrate synthase activity in muscle. In other embodiments, the increase of muscular endurance is an increase of aerobic endurance. In another embodiment, the increase of aerobic endurance is an increase in the proportion of Type I fibers in muscle. In one embodiment, the strain of *Bacillus pumilus* species is a strain of *Bacillus pumilus* species with deposit number LMG P-28202.

An additional aspect of this invention refers to a method of increasing the adiponectin levels, increasing the mitochondrial activity in muscle, increasing muscular endurance, stimulating wound healing and/or reepithelialization of the skin, stimulating collagen synthesis and/or hyaluronic acid synthesis, treatment and/or prevention of skin aging, treatment and/or prevention of skin wrinkles, treatment of skin firming and/or prevention of loss of skin firmness which comprises the administration of a cosmetically or dermopharmaceutically effective quantity of the ferment extract of a strain of *Bacillus pumilus* species. In one embodiment, the adiponectin level is the level of circulating adiponectin. In other embodiment, the adiponectin level is adiponectin level in adipocytes. In one embodiment, the increase of mitochondrial activity in muscle is an increase of the level of ATP and/or citrate synthase activity in muscle. In other embodiment, the increase of muscular endurance is an increase of aerobic endurance. In other embodiment, the increase of aerobic endurance is an increase in the proportion of Type I fibers in muscle. In one embodiment, the strain of *Bacillus pumilus* species is a strain of *Bacillus pumilus* species with deposit number LMG P-28202. In another embodiment, the increase of mitochondrial activity in muscle, increase of muscular endurance, stimulation of wound healing and/or reepithelialization of the skin are a consequence of the increase of the adiponectin level. In another embodiment, the treatment and/or prevention of skin aging, treatment and/or prevention of skin wrinkles, treatment of skin firming and/or prevention of loss of skin firmness are a consequence of collagen synthesis stimulation.

In one embodiment, the increase of adiponectin levels causes an increase in the mitochondrial activity in muscle, increase of muscular endurance, stimulation of wound healing and/or reepithelialization of the skin, stimulation of collagen synthesis and/or hyaluronic acid synthesis, treatment and/or prevention of skin aging, treatment and/or prevention of skin wrinkles, treatment of skin firming and/or prevention of loss of skin firmness.

In another aspect, the ferment extract produced by a strain of *Bacillus pumilus* species is administered by any means that causes its contact with the site of action in the human being, and often, in the form of a composition which contains it. The administration of the ferment extract produced by a strain of *Bacillus pumilus* species is carried out topically or transdermally. In one embodiment, the topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of the application or administration can vary widely, depending on the needs of each subject, suggesting a range of application or administration from once per month to 10 times per day, from once per week to 4 times per day, from three times per week to three times per day, or once per day.

Deposit of Biological Material

The strain of the *Bacillus pumilus* species was deposited at the Belgian Coordinated Collection of Microorganisms (BCCM)/Laboratorium voor Microbiologie-Bacteriëverzameling (LMG) (University Ghent, K. L. Ledeganckstraat 35, 9000 Ghent, Belgium) under the conditions of the Budapest Treaty. The deposit was done on Mar. 11, 2014 and the deposit number was LMG P-28202.

EXAMPLES

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as approximated, i.e., subject to a variability of ±5%, ±3%, ±1%, ±0.1%, or ±0.01% over the indicated value. It is to be understood that the upper and lower amount, range, and ratio limits set forth herein may be independently combined. Similarly, the ranges and amounts for each element of the technology described herein can be used together with ranges or amounts for any of the other elements.

Example 1

Obtaining the Ferment Extract of a Strain of *Bacillus pumilus* Species with Deposit Number LMG P-28202

A) Culture Process of the *Bacillus pumilus* Strain with Deposit Number LMG P-28202.

The *Bacillus pumilus* strain with deposit number LMG P-28202 is cultured in a bioreactor, at 25° C. and a pH of 8.0, in a culture medium containing water, 1 g/L of yeast extract and 4 g/L of peptone as carbon and nitrogen sources, 20 g/L of glucose as additional carbon source, and sea salts at a concentration of 31 g/L. It is inoculated from an exponentially growing preculture at an optical density of 0.2 AU at 600 nm wavelength. The fermentation is extended to 72 hours of culture. The dissolved oxygen concentration is controlled at 30% saturated air and the stirring is maintained at values around 200 rpm.

B) Purification of the Ferment Extract Obtained from the *Bacillus pumilus* Strain with Deposit Number LMG P-28202.

The bacteria are separated from the resulting fermentation broth described in example 1a) containing the ferment extract by continuous centrifugation with a Westfalia CSA-1 centrifuge, working at 10,000 rpm. The removal of bacteria is completed by filtration at a final pore size of 0.2 μm. Subsequently the resulting supernatant containing the ferment extract is freeze-dried.

Example 2

Physicochemical Characterization of the Ferment Extract of the *Bacillus pumilus* Strain with Deposit Number LMG P-28202

For the physicochemical characterization of the ferment extract of a strain of the *Bacillus pumilus* species with deposit number LMG P-28202, obtained according to the example 1, High Performance Liquid Chromatography (HPLC), primary amines (Ninhydrin test), secondary amines (Chloranyl Assay) carbohydrate (Fehling), and phenol (Folin-Ciocalteau) assays are performed.

Chromatographic Analysis SE-HPLC-UV

A solution of the ferment extract obtained according to example 1 in water:glycerin (9:95) at 7 mg/mL is prepared and analyzed by HPLC-UV. A dilution 1:5 with water is done previously and filtered through 0.22 μm cellulose acetate filter. 100 μL are injected in a High Performance Liquid Chromatography (HPLC) LC20A SHIMADZU. The chromatographic column used is TSKGel G2000SWXL, 5 m, 125 Å, 7.8 mm×30 mm (TOSOH Bioscience) and water with 0.1M pH=6.70+0.1M phosphate buffer+0.1M sodium sulfate as eluent.

Under these conditions, the chromatogram of the product shows peaks between 10 and 15 minutes, with a mean peak at 11 minutes, in between the retention times of the standards aminobenzoic acid (MW=137 Da) and Ribonuclease A from bovine pancreas (MW=13700 Da).

Primary Amines (Ninhydrin Assay)

Reagents: Ninhydrin Reagent A: 40 g of phenol are dissolved in 10 mL of absolute ethanol. In parallel, 65 mg of KCN are dissolved in 100 mL of water. 2 mL of this solution are dissolved in 100 mL of pyridine distilled through ninhydrin. Both solutions are mixed with 4 g of Amberlite® MB-3 during 45 minutes. Finally, the solution is filtered through paper and then mixed. Ninhydrin Reagent B: 2.5 mg of ninhydrin are dissolved in 50 mL of absolute ethanol.

Method: 0.5 mL of a 1 mg/mL aqueous solution of the ferment extract obtained according the example 1 are poured into a 2 mL tube. Then 3 droplets of Ninhydrin Reagent A and 1 droplet of Ninhydrin Reagent B are added to the tube and mixed. Then, it is kept at 110° C. during 2 minutes. The analyzed product shows yellow color, therefore indicating that primary amines are not detected. After acid hydrolysis for 4 hours with 4M TFA solution, the Ninhydrin test is repeated, obtaining a positive result, which indicated that the ferment extract contains amino acids in peptidic form.

Secondary Amines (Chloranyl Assay)

Reagents: Acetone, and Chloranil reaction Reagent: 0.75 g of chloranyl (2,3,5,6-tetrachloro-1,4-benzoquinone) are dissolved in 25 mL of toluene in order to obtain a saturated solution.

Method: 4 droplets of acetone are added to 20 mg of a freeze-dried ferment extract obtained according to example 1. Then, 1 droplet of Chloranyl Reaction Reagent is added. This mixture is stirred and kept at room temperature for 5 minutes. The analyzed product does not developed green-blue coloration, therefore indicating that no secondary amines are detected in the ferment extract.

Carbohydrate Analysis (Fehling Assay)

Reagents: Fehling A: 48.3 g of copper (II) sulfate in 1 L of water with 1 mL of sulfuric acid 96%. Fehling B: 90 g of sodium hydroxide with 300 g of potassium sodium tartrate in 1 L of water.

Method: 1 mL of reagent Fehling A and 1 mL of reagent Fehling B are added to 10 mg of the ferment extract obtained according to the example 1, and the sample is heated at 60° C. for 45-60 min. A red solid precipitate indicates the presence of reductive carbohydrates in the ferment extract.

Phenol Assay (Folin-Ciocalteau Assay)

Reagents: Folin-Ciocalteau reagent (from Sigma-Aldrich; Ref. 47641); $Na_2CO_3$ (from Panreac) and Methanol (from Scharlab).

Method: In a 10 ml tube the following reagents are added: 0.5 ml of 1 mg/ml of a water solution of the ferment extract obtained according to the example 1, 0.5 ml of Folin-Ciocalteau reagent, 1.5 ml of $Na_2CO_3$ 20% and 7 mL of Methanol:Water (1:1). This solution is kept in the dark for 1 hour. The same solution is prepared as a blank without the ferment extract (replaced with water). Negative result, colorless solution indicates that no phenols are detected in the ferment extract.

Example 3

Preparation of a Cosmetic Cream Composition Comprising the Ferment Extract of the Strain of the *Bacillus pumilus* Species with Deposit Number LMG P-28202

In an appropriate container, water [INCI: WATER (AQUA)], potassium sorbate [INCI: POTASSIUM SORBATE], and disodium EDTA [INCI: DISODIUM EDTA] are mixed and stirred until solubilization is achieved. Next, Carbopol® Ultrez 20 [INCI: CARBOMER] is added and stirred to total dispersion. Afterwards, xanthan gum [INCI: XANTHAN GUM], is added and also stirred until total dispersion. This mixture of ingredients constitutes phase A.

The ingredients from B phase Hydrolite®5 2/016020 [INCI: PENTYLENE GLYCOL], Zemea® [INCI: PROPANEDIOL], and phenoxyethanol [INCI: PHENOXYETHANOL], are added, one by one to the phase A mixture, under stirring.

The phase C, which comprised cyclohexasiloxane BRB CM60™ [INCI: CYCLOHEXASILOXANE] is added to the mixture of phase A and phase B, stirring until homogenization.

The ingredient from phase D Schercemol™ 1818 [INCI: ISOSTEARYL ISOSTEARATE] is added to the previous mixture under stirring, until it is totally incorporated into the mixture.

Phase E comprises the ferment extract obtained according to example 1 from the *Bacillus pumilus* strain with deposit number LMG P-28202, glycerin [INCI: GLYCERIN], water [INCI: WATER (AQUA)]. This phase is added to the mixture of ingredients of the phases A, B, C and D under stirring until solubilization.

Likewise, the ingredient from phase F Diffuporine® [INCI: ACETYL HEXAPEPTIDE-37, BUTYLENE GLYCOL, WATER (AQUA)] is added to the previous mixture until solubilization.

The phase G ingredient ethyl alcohol [INCI: ALCOHOL DENAT.] is added under stirring.

Subsequently, the perfume Vitamin Cocktail [INCI: FRAGRANCE (PARFUM)] (phase H) is added under stirring.

The pH is adjusted to 6.0-6.5 by addition of sodium hydroxide [INCI: SODIUM HYDROXIDE] (q.s sufficient quantity to adjust to this pH) under stirring (phase I), obtaining a cosmetic composition with the proportions shown in table 1.

TABLE 1

| | INGREDIENT | % weight |
|---|---|---|
| A | WATER (AQUA) | 68.050 |
| A | CARBOMER | 0.550 |
| A | DISODIUM EDTA | 0.200 |
| A | POTASSIUM SORBATE | 0.100 |
| A | XANTHAN GUM | 0.050 |
| B | PROPANEDIOL | 10.00 |
| B | PENTYLENE GLYCOL | 2.500 |
| B | PHENOXYETHANOL | 0.350 |
| C | CYCLOHEXASILOXANE | 4.000 |
| D | ISOSTEARYL ISOSTEARATE | 2.000 |
| E | Ferment extract obtained according to example 1 | 0.004 |
| E | WATER (AQUA) | 0.246 |
| E | GLYCERIN | 4.750 |
| F | BUTYLENE GLYCOL | 1.000 |
| F | WATER (AQUA) | 0.999 |
| F | ACETYL HEXAPEPTIDE-37 | 0.001 |
| G | ALCOHOL DENAT. | 5.000 |
| H | FRAGRANCE (PARFUM) | 0.200 |
| I | SODIUM HYDROXIDE 20% | q.s. |

Example 4

Preparation of a Cosmetic Cream Composition Comprising the Ferment Extract of the Strain of the *Bacillus pumilus* Species with Deposit Number LMG P-28202

In an appropriate container, water [INCI: WATER (AQUA)], Hydrolite®5 [INCI: PENTYLENE GLYCOL], glycerin [INCI: GLYCERIN], Betain BP [INCI: BETAINE], and Microcare BNA [INCI: BENZYL ALCOHOL] are mixed and stirred until solubilization. Subsequently, Carbopol® Ultrez 10 [INCI: CARBOMER] is added and stirred until dispersion. Then, Arlatone™ MAP 160K [INCI: POTASSIUM CETYL PHOSPHATE] is added and stirred until its total dispersion. This mixture of ingredients constitutes phase A.

Next, the phase B ingredients cetyl alcohol [INCI: CETYL ALCOHOL], Finsolv® TN [INCI: C12-C15 ALKYL BENZOATE], Massocare™ HD [INCI: ISOHEXADECANE], Polysorbate 20 [INCI: POLYSORBATE 20], stearic acid [INCI: STEARIC ACID] and phenoxyethanol [INCI: PHENOXYETHANOL] are mixed and warmed to 70° C.

Phases A and B are mixed at 70° C. under stirring.

Then, the mixture of A and B is cooled to 40° C., and the ingredient from phase C Silicone DC 345 fluid [INCI: CYCLOMETHICONE] is added at this temperature and stirred until total homogenization of the mixture.

Phase D ingredient, comprising the ferment extract of the strain of the *Bacillus pumilus* species with deposit number LMG P-28202 obtained according to example 1, glycerin

[INCI: GLYCERIN] and water [INCI: WATER (AQUA)], are added under stirring until homogenization.

Subsequently, the perfume [INCI: FRAGRANCE (PARFUM)] (phase E) is added under stirring. The pH is adjusted to 6.0-6.5 by addition of sodium hydroxide [INCI: SODIUM HYDROXIDE] (q.s. sufficient quantity to adjust to this pH) under stirring (phase F), obtaining a cosmetic composition with the proportions shown in table 2.

TABLE 2

| | INGREDIENT | % weight |
|---|---|---|
| A | WATER (AQUA) | 75.335 |
| A | PENTYLENE GLYCOL | 4.750 |
| A | GLYCERIN | 2.850 |
| A | BETAINE | 2.850 |
| A | BENZYL ALCOHOL | 0.380 |
| A | CARBOMER | 0.285 |
| A | POTASSIUM CETYL PHOSPHATE | 0.380 |
| B | CETYL ALCOHOL | 1.710 |
| B | C12-C15 ALKYL BENZOATE | 1.425 |
| B | ISOHEXADECANE | 0.950 |
| B | POLYSORBATE 20 | 0.760 |
| B | STEARIC ACID | 0.475 |
| B | PHENOXYETHANOL | 0.855 |
| C | CYCLOMETHICONE | 1.900 |
| D | Ferment extract obtained according to example 1 | 0.004 |
| D | WATER (AQUA) | 0.246 |
| D | GLYCERIN | 4.750 |
| E | FRAGRANCE (PARFUM) | 0.095 |
| F | SODIUM HYDROXIDE 20% | q.s. |

Example 5

Preparation of a Microemulsion Comprising the Ferment Extract of the Strain of the *Bacillus pumilus* Species with Deposit Number LMG P-28202

In an appropriate container, Docusate Sodium USP [INCI: DIETHYLHEXYL SODIUM SULFOSUCCINATE] and isostearic acid [INCI: ISOSTEARIC ACID] are mixed (phase A).

In another container, a mixture comprising the ferment extract of the strain of the *Bacillus pumilus* species with deposit number LMG P-28202 obtained according to example 1, glycerin [INCI: GLYCERIN], and water [INCI: WATER (AQUA)], is dissolved in ethanol [INCI: ALCOHOL] (phase B). Slowly, phase B is added to phase A under stirring. See table 3.

TABLE 3

| | INGREDIENT | % weight |
|---|---|---|
| A | DIETHYLHEXYL SODIUM SULFOSUCCINATE | 13.500 |
| A | ISOSTEARIC ACID | 76.500 |
| B | GLYCERIN | 6.650 |
| B | WATER (AQUA) | 0.345 |
| B | Ferment extract obtained according to example 1 | 0.005 |
| B | ALCOHOL | 3.000 |

Example 6

Preparation of a Lipid Nanoparticle Composition Comprising the Microemulsion of Example 5

Water [INCI: WATER (AQUA)], Amigel® [INCI: SCLEROTIUM GUM], Zemea™ [INCI: PROPANEDIOL], ZEMEA® [INCI: PROPANEDIOL], and phenoxyethanol [INCI: PHENOXYETHANOL] (phase A ingredients) are added in that order to an appropriate container and stirred until homogeneity is achieved.

The mixture comprising the microemulsion of example 5, refined soybean oil IP Ph. Eur. [INCI: *GLYCINE SOJA* (SOYBEAN) OIL], Arlacel® 83 [INCI: SORBITAN SESQUIOLEATE], and Arlamol™ HD [INCI: ISOHEXADECANE] (phase B ingredients) is added to another container.

Then, the mixture of the phase B ingredients is added to the mixture of the phase A ingredients under turbine stirring until an emulsion is formed. Subsequently, the mixture is homogenized with a titanium probe for one minute.

Then, dropwise and under stirring, a water [INCI: WATER (AQUA)] suspension of SENSOMER™ CT-400 [INCI: *CASSIA* HYDROXYPROPYLTRIMONIUM CHLORIDE] is added (phase C INGREDIENTS). See table 4.

TABLE 4

| | INGREDIENT | % WEIGHT |
|---|---|---|
| A | WATER (AQUA) | q.s.100 |
| A | SCLEROTIUM GUM | 0.50 |
| A | PROPANEDIOL | 5.00 |
| A | PHENOXYETHANOL | 2.6 |
| B | Microemulsion of example 5 | 8.00 |
| B | GLYCINE SOJA (SOYBEAN) OIL | 12.00 |
| B | SORBITAN SESQUIOLEATE | 4.30 |
| B | ISOHEXADECANE | 5.50 |
| C | WATER (AQUA) | 2.00 |
| C | SENSOMER ™ CT-400 (CASSIA HYDROXYPROPYLTRIMONIUM CHLORIDE, WATER (AQUA) | 0.20 |

Example 7

Preparation of Liposomes Comprising the Ferment Extract of the Strain of the *Bacillus pumilus* Species with Deposit Number LMG P-28202

In an appropriate container, water [INCI: WATER (AQUA)], Zemea™ [INCI: PROPANEDIOL] and phenoxyethanol [INCI: PHENOXYETHANOL] (phases B to D) are added to phase A mixture, which comprised the ferment extract of the strain of the *Bacillus pumilus* species with deposit number LMG P-28202 obtained according to example 1, glycerin [INCI: GLYCERIN], and water [INCI: WATER (AQUA)].

When all the previous components are dissolved, Leciflor™ 100 IP [INCI: LECITHIN] (phase E) is added little by little and under intense stirring, until complete solution. Then, Labrasol® [INCI: PEG-8 CAPRYLIC/CAPRIC GLYCERIDES] (phase F) is added and stirred for 10-15 minutes to form an emulsion. The finally obtained composition is shown in table 5.

TABLE 5

| | INGREDIENT | % weight |
|---|---|---|
| A | GLYCERIN | 9.500 |
| A | WATER (AQUA) | 0.493 |
| A | Ferment extract obtained according to example 1 | 0.007 |
| B | WATER (AQUA) | q.s. 100 |
| C | PROPANEDIOL | 8.500 |
| D | PHENOXYETHANOL | 1.700 |

TABLE 5-continued

| INGREDIENT | | % weight |
|---|---|---|
| E | LECITHIN | 10.000 |
| F | PEG-8 CAPRYLIC/CAPRIC GLYCERIDES | 4.000 |

The sample is homogenized with a titanium probe for 30 seconds.

Example 8

Preparation of Liposomes of Example 7 Bound to Cationic Polymers

The liposomes obtained in example 7 are added to SENSOMER® CT-50 [INCI: WATER (AQUA), STARCH HYDROXYPROPYLTRIMONIUM CHLORIDE, UREA, SODIUM LACTATE, SODIUM CHLORIDE, SODIUM BENZOATE] at a liposomes:cationic polymer ratio of 95:5 under slow stirring.

Example 9

Study of the Relative Increase in the Adiponectin Protein Level from Primary Human Subcutaneous Preadipocytes by a Colorimetric ELISA Assay (Enzyme-Linked Immunosorbent Assay)

The relative increase in the adiponectin protein level is determined in primary human adipocytes after treatment with the ferment extract of a strain of Bacillus pumilus species with deposit number LMG P-28202 obtained in accordance with example 1 in Adipocyte Differentiation Medium. Cells treated only with Adipocyte differentiation Medium are used as basal control.

Human preadipocytes are seeded (10,000 cells/well, 3 wells per condition) in 96-clear well plates in Preadipocyte Growth Medium and cells are incubated for 24 hours at 37° C. in a water-saturated atmosphere of 95% air and 5% $CO_2$. After incubation, the medium is removed and cells are incubated with the ferment extract obtained in accordance with example 1 at 5 µg/ml in Adipocyte Differentiation Medium in order to induce differentiation of preadipocytes into adipocytes (8 days at 37° C. and 5% $CO_2$). Then, culture supernatants are harvested, the amount of released adiponectin is determined by ELISA, and the total cell number per well is quantified by Crystal Violet staining assay. ELISA results are normalized with the total cell number for the treatment condition and the relative increase in the adiponectin protein level is calculated respect to the basal control.

Quantification of Adiponectin Levels by ELISA

An Adiponectin ELISA Assay kit is used following manufacturer's instructions (R&D Systems). Briefly, culture supernatants are incubated in a microtiter plate pre-coated with an adiponectin capture antibody. Afterwards, wells are incubated with another specific adiponectin detection biotin-conjugated antibody. Then, Streptavidin-HRP (enzyme Horseradish Peroxidase conjugated to the Streptavidin) is added to the plate. Finally, the substrate TMB (Tetramethylbenzidine) is added and a color change is developed, directly proportional to the amount of adiponectin present in the tested dose. The reaction is stopped with a sulfuric acid solution and the absorbance is read in a Microplate Absorbance Reader (Multiskan-Thermo Electro Corporation) at 450 nm with wavelength correction at 570 nm.

Determination of the Total Cell Number by Crystal Violet Staining Assay

Plates containing cells (after supernatants are harvested for ELISA assay) are incubated with Crystal Violet solution. DNA of the cells is stained by Crystal Violet dye solution. Afterwards, Crystal Violet solution is removed and the wells are washed with Milli-Q™ water. The amount of Crystal Violet dye taken by up by the cells is directly proportional to the number of cells in each well. Finally, when cells are dried, an HCl solution is added and absorbance read at 630 nm in a Microplate Absorbance Reader (Multiskan-Thermo Electro Corporation). ELISA results are normalized with the total cell number for the tested dose, and the relative increase in the adiponectin protein level is calculated respect to the basal control, table 6.

TABLE 6

| Treatment | Tested dose | Relative level of adiponectin respect to basal control |
|---|---|---|
| Ferment extract of Bacillus pumilus strain from example 1 | 5 µg/mL | +68.34% ± 5.32% |

The result shows that the ferment extract of a strain of the Bacillus pumilus species with deposit number LMG P-28202 obtained in accordance with example 1 increases the relative adiponectin level in human adipocytes cell cultures at the tested dose.

Example 10

Study of the Relative Increase of Myosin Protein Expression in Human Skeletal Muscle Cells by Immunofluorescence The expression of slow skeletal Myosin Heavy Chain 7 (MYH7) is studied in human skeletal muscle cells treated with supernatant of an adipocyte culture after treatment with the ferment extract obtained in accordance with example 1 in Adipocyte Differentiation Medium. Human skeletal muscle cells treated only with supernatants of an adipocyte culture non-treated with ferment extract are used as basal control.

Human skeletal muscle cells are seeded (10,000 cells/well, 2 wells per each tested dose) in 12-clear well plate with coverslips pre-coated with coating Matrix in Muscle Cellutions Growth Medium and the cells are incubated for 48 h. After 24 h, the differentiation process is initiated by adding Muscle Cellutions Differentiation Medium.

After 10 days of differentiation, the medium is removed and cells are treated during 48 h at 37° C. in an atmosphere with 5% $CO_2$ with the supernatants of an adipocyte culture that has been treated for 8 days with the ferment extract obtained in accordance with example 1 (5 µg/ml in Adipocyte Differentiation Medium). The amount of adiponectin in supernatants of adipocyte culture is determined by an ELISA test using specific antibodies.

Determination of the Expression of Myosin Protein

After treatment, cells are washed with Phosphate Buffer Saline (PBS) and fixed with 4% Paraformaldehyde (PFA). After this step, cells are incubated with a primary mouse monoclonal antibody to Anti-Slow Skeletal Myosin Heavy Chain 7 (MYH7) antibody overnight at 4° C. On the next day, cells are washed with PBS, and secondary Alexa Fluor® 594 goat anti-mouse IgG (H+L) antibody (red fluorescence emission dye) is incubated with their primary antibodies for 1 h in the dark. Then, cells are stained with DAPI (4',6-diamino-2-phenylindole) and mounted in the darkness.

Cells are observed using a Zeiss fluorescence microscopy and images are captured using Zen software. To verify that cell number in all tested dose is superimposable, nuclei are revealed with DAPI staining and 10 representative images from each tested dose are collected. From each fluorescence image of myosin, values of ID (Integrated Density) are quantified. ImageJ software is used. Two independent assays in duplicate are performed. Relative increase of myosin level is normalized respect to the basal control, table 7.

TABLE 7

The results obtained show that supernatants of adipocyte cultures

| Treatment | Tested dose | Relative induction of MYH7 protein respect to basal control |
|---|---|---|
| Ferment extract of *Bacillus pumilus* strain from example 1 | 5 µg/mL | +69.78 ± 16.34% | containing high levels of adiponectin after treatment with the ferment extract obtained in accordance with example 1 at 5 µg/ml are able to enhance the expression levels of protein Myosin up 69.78% with respect to basal control.

Example 11

Study of the Relative Increase in the Citrate Synthase Activity in Primary Human Skeletal Muscle Cells Treated with Supernatants of an Adipocyte Culture Containing Adiponectin The relative increase in the citrate synthase activity is determined in human skeletal muscle cells treated with supernatant of an adipocyte culture after treatment with the ferment extract obtained in accordance with example 1 in Adipocyte Differentiation Medium. Human skeletal muscle cells treated with a supernatant of an adipocyte culture non-treated with the ferment extract are used as basal control.

Human skeletal muscle cells are seeded (200,000 cells/well, 2 wells per tested dose) in 6-clear well plates in Muscle Cellutions Growth Medium and the cells are incubated for 48 hours at 37° C. in a water-saturated atmosphere of 95% air and 5% $CO_2$. Then, the differentiation process is initiated by adding Muscle Cellutions Differentiation Medium. After 72 hours of differentiation, the medium is removed and cells are incubated with supernatants of an adipocyte culture containing a high level of adiponectin, previously determined by ELISA, after 8 days of treatment with ferment extract obtained in accordance with example 1 (5 µg/ml in Adipocyte Differentiation Medium). After 48 hours of treatment at 37° C. in a $CO_2$ incubator, human skeletal muscle cells are lysed and their total protein content determined by BCA assay (Bicinchoninic Acid). All lysates are diluted to the same final total protein concentration determined by BCA assay, and the relative increase in the citrate synthase activity is quantified respect to the basal control.

Total Protein Determination by BCA Assay

A BCA assay kit is used following manufacturer's instructions (Thermo Scientific). The total protein concentration of the human skeletal muscle cell lysates is determined by a colorimetric reaction using a standard of Bovine Serum Albumin (BSA). Briefly, standards and samples are dispensed into a 96-clear well plate. After incubation with the working reagent, the absorbance is measured at 570 nm in a Microplate Absorbance Reader (Multiskan-Thermo Electro Corporation).

Measurement of Citrate Synthase Activity

A citrate synthase assay kit is used following manufacturer's instructions (Sigma). Briefly, cell lysates are incubated in a 96-clear well plate with a reaction mixture containing acetyl-coenzyme A and DTNB (5,5'-dithiobis-(2-nitrobenzoic acid)). Then, oxaloacetate, which is a citrate synthase substrate, is added and a colour change is developed, directly proportional to the citrate synthase activity in the tested dose. Absorbance is read in a Microplate Absorbance Reader (Multiskan-Thermo Electro Corporation) at 405 nm. Relative increase of citrate synthase activity is normalized respect to the basal control, Table 8.

TABLE 8

| Treatment | Tested dose | Relative level of citrate synthase activity respect to basal control |
|---|---|---|
| Ferment extract of *Bacillus pumilus* strain from example 1 | 5 µg/mL | +47.85% ± 3.35% |

The results show that the bacterial extracellular substance obtained from the *Bacillus* sp. strain with deposit number LMG P-28202 obtained in accordance with example 1 is able to increase the relative citrate synthase activity in human skeletal muscle cells at the tested dose.

Example 12

Study of the Relative Increase in the ATP Production in Primary Human Skeletal Muscle Cells Treated with Supernatants of an Adipocyte Culture Containing Adiponectin The relative increase in the ATP production is determined in human skeletal muscle cells treated with supernatant of an adipocyte culture after treatment with the ferment extract obtained in accordance with example 1 in Adipocyte Differentiation Medium. Human skeletal muscle cells treated with a supernatant of an adipocyte culture non-treated with the ferment extract are used as basal control.

Human skeletal muscle cells are seeded (200,000 cells/well, 2 wells per tested dose) in 6-clear well plates in Muscle Cellutions Growth Medium and cells are incubated for 48 hours at 37° C. in a water-saturated atmosphere of 95% air and 5% $CO_2$. Then, the differentiation process is initiated by adding Muscle Cellutions Differentiation Medium. After 72 hours of differentiation, the medium is removed and cells are incubated with supernatants of an adipocyte culture containing a high level of adiponectin, previously determined by ELISA, after 8 days of treatment with ferment extract obtained in accordance with example 1 (5 µg/ml in Adipocyte Differentiation Medium). After 48 hours of treatment at 37° C. in a $CO_2$ incubator, human skeletal muscle cells are lysed and ATP produced is quantified by a specific assay kit and the total protein content determined by BCA. ATP results are normalized with the total protein concentration for the tested dose, and the relative increase in the produced ATP is quantified respect to the basal control.

Measurement of ATP Production

An ATP Assay kit is used following manufacturer's instructions (Abcam). Briefly, cell lysates are incubated in a 96-clear well plate with a reaction mixture containing ATP Probe, ATP Converter, Developer Mix and ATP Assay Buffer to generate a product that is quantified by fluorescence with an Automated Plate Fluorescence Reader (Clariostar®-BMG) set for excitation at 530 nm and detection at 590 nm.

Total Protein Determination by BCA Assay

A BCA Assay kit is used following manufacturer's instructions (Thermo Scientific). The total protein concentration of the human skeletal muscle cell lysates is determined by a colorimetric reaction using a standard of Bovine Serum Albumin (BSA). Briefly, standards and samples are dispensed into a 96-clear well plate. After incubation with the working reagent, the absorbance is measured at 570 nm in a Microplate Absorbance Reader (Clariostar®-BMG). ATP results are normalized with the total protein concentration for the tested dose, and the relative increase in the produced ATP is quantified respect to the basal control, Table 9.

TABLE 9

| Treatment | Tested dose | Relative level of produced ATP respect to basal control |
|---|---|---|
| Ferment extract of *Bacillus pumilus* strain from example 1 | 5 µg/mL | +136.00% ± 5.45% |

The results show that the bacterial extracellular substance obtained from the *Bacillus* sp. strain with deposit number LMG P-28202 obtained in accordance with example 1 is able to increase the relative ATP production in human skeletal muscle cells at the tested dose.

Example 13

Study of the Profile of the Gene Expression of Primary Human Subcutaneous Preadipocytes Human subcutaneous preadipocytes are seeded at a density of 130,000 cells/well in 12 well plates in PGM-2 (Basal medium PBM-2 supplemented with 10% FBS, 2 mM L-Glutamine and 100 units/mL gentamicin/anfotericine) and cells are incubated for 24 hours at 37° C. in a water-saturated atmosphere of 95% air and 5% $CO_2$.

After 24 h, the medium is removed and the cells are incubated for 8 days at 37° C. in a $CO_2$ incubator with the ferment extract obtained in accordance with example 1 at 14 µg/ml in differentiation medium PDM-2 (PGM-2 supplemented with insulin, dexamethasone, indomethacin and IBMX) or only with PDM-2 (basal control). The ferment extract obtained in accordance with example 1 and the basal control are assayed in 4 biological replicates (wells).

Then, the cells are lysed and the RNA is extracted and purified from each replica and each tested dose by means of the RNeasyPlus™ Mini kit by Qiagen. The cell lysates are homogenized and the RNases are inactivated. The genomic DNA is removed from the samples by using gDNA Eliminator spin columns of the RNeasyPlus™ Mini kit. Then, the samples are passed through special RNA binding columns of the RNeasyPlus™ Mini kit and after several microcentrifugation washes, the purified RNA is eluted with 50 µl of ultrapure water.

The purity, integrity and concentration of the RNA obtained are evaluated by means of spectrophotometry (Nanodrop) and with a bioanalyzer (Agilent Bioanalyzer). Later, the samples are labelled and hybridized in a human gene expression microarray (SurePrint G3, Agilent).

The normalized values obtained for the tested dose are compared with the normalized values obtained for the basal control to determine genes with differential expression. Next, a parametric analysis of the data is carried out by means of the Bioconductor software.

The values obtained are then evaluated by means of GSEA (Gene Set Analysis Enrichment) to group together the genes with differential expression in terms of Gene Ontology and Biological Routes. The results obtained are shown in table 10.

TABLE 10

| Symbol | Gene Name | % Fold induction |
|---|---|---|
| Genes involved in glucose metabolism downregulated by the ferment extract obtained in accordance with example 1 | | |
| ARF6 | ADP-ribosylation factor 6 | −23.41 |
| CRK | v-crk avian sarcoma virus CT10 oncogene honnolog | −25.36 |
| FOS | FBJ murine osteosarcoma viral oncogene homolog | −28.28 |
| IRS1 | insulin receptor substrate 1 | −18.52 |
| IRS2 | insulin receptor substrate 2 | −20.65 |
| MAP2K1 | mitogen-activated protein kinase kinase 1 | −39.58 |
| MAP3K1 | mitogen-activated protein kinase kinase kinase 1, E3 ubiquitin protein ligase | −19.25 |
| ME1 | malic enzyme 1, NADP(+)-dependent, cytosolic | −27.66 |
| ATP6V0E1 | ATPase, H+ transporting, lysosomal 9 kDa, V0 subunit e1 | −20.34 |
| ATP6V1A | ATPase, H+ transporting, lysosomal 70 kDa, V1 subunit A | −19.81 |
| ATP6V1B2 | ATPase, H+ transporting, lysosomal 56/58 kDa, V1 subunit B2 | −21.33 |
| ATP6V1E1 | ATPase, H+ transporting, lysosomal 31 kDa, V1 subunit E1 | −27.67 |
| ATP6V1H | ATPase, H+ transporting, lysosomal 50/57 kDa, V1 subunit H | −26.05 |
| ENO1 | enolase 1, (alpha) | −22.7 |
| HK3 | hexokinase 3 (white cell) | −21.03 |
| LDHA | lactate dehydrogenase A | −36.14 |
| LDHB | lactate dehydrogenase B | −18.19 |
| PGAM1 | phosphoglycerate mutase 1 (brain) | −20.16 |
| PCK1 | phosphoenolpyruvate carboxykinase 1 (soluble) | −19.38 |
| DLAT | dihydrolipoamide S-acetyltransferase | −24.71 |
| FH | fumarate hydratase | −26.03 |
| IDH1 | isocitrate dehydrogenase 1 (NADP+), soluble | −27.61 |
| IDH2 | isocitrate dehydrogenase 2 (NADP+), mitochondrial | −25.75 |

TABLE 10-continued

| Symbol | Gene Name | % Fold induction |
|---|---|---|
| IDH3B | isocitrate dehydrogenase 3 (NAD+) beta | −20.46 |
| SDHB | succinate dehydrogenase complex, subunit B, iron sulfur (Ip) | −30.26 |
| SDHD | succinate dehydrogenase complex, subunit D, integral membrane protein | −23.84 |
| SUCLA2 | succinate-CoA ligase, ADP-forming, beta subunit | −33.26 |
| GFPT1 | glutamine-fructose-6-phosphate transaminase 1 | −22.05 |
| PGD | phosphogluconate dehydrogenase | −38.17 |
| Mitochondrial genes downregulated by the ferment extract obtained in accordance with example 1 | | |
| ATP5A1 | ATP synthase, H+ transporting, mitochondrial F1 complex, alpha subunit 1, cardiac muscle | −33.39 |
| ATP5B | ATP synthase, H+ transporting, mitochondrial F1 complex, beta polypeptide | −29.47 |
| ATP5C1 | ATP synthase, H+ transporting, mitochondrial F1 complex, gamma polypeptide 1 | −22.99 |
| COX4I1 | cytochrome c oxidase subunit IV isoform 1 | −20.03 |
| CYC1 | cytochrome c-1 | −22.14 |
| CYCS | cytochrome c, somatic | −23.37 |
| HADH | hydroxyacyl-CoA dehydrogenase | −20.05 |
| HADHA | hydroxyacyl-CoA dehydrogenase/3-ketoacyl-CoA thiolase/enoyl-CoA hydratase (trifunctional protein), alpha subunit | −26.12 |
| HADHB | hydroxyacyl-CoA dehydrogenase/3-ketoacyl-CoA thiolase/enoyl-CoA hydratase (trifunctional protein), beta subunit | −17.67 |
| SLC25A20 | solute carrier family 25 (carnitine/acylcarnitine translocase), member 20 | −19.94 |
| Genes implicated in adipogenesis process downregulated by the ferment extract obtained in accordance with example 1 | | |
| AGT | angiotensinogen (serpin peptidase inhibitor, clade A, member 8) | −17.35 |
| EGR2 | early growth response 2 | −25.04 |
| IRS1 | insulin receptor substrate 1 | −18.52 |
| IRS2 | insulin receptor substrate 2 | −20.65 |
| KLF5 | Kruppel-like factor 5 (intestinal) | −18.13 |
| LPL | lipoprotein lipase | −22.15 |
| NCOA3 | nuclear receptor coactivator 3 | −22.59 |
| PCK1 | phosphoenolpyruvate carboxykinase 1 (soluble) | −19.38 |
| PPARG | peroxisome proliferator-activated receptor gamma | −19.86 |
| TNF | tumor necrosis factor | −17.63 |
| Genes involved in triglycerides synthesis downregulated by the ferment extract obtained in accordance with example 1 | | |
| DGAT2 | diacylglycerol O-acyltransferase 2 | −45.5 |
| LPL | lipoprotein lipase | −22.15 |
| PPAP2A | phosphatidic acid phosphatase type 2A | −23.3 |
| PPAP2B | phosphatidic acid phosphatase type 2B | −30.62 |
| Other genes downregulated by the ferment extract obtained in accordance with example 1 | | |
| SH2B1 | SH2B adaptor protein 1 | −23.43 |
| SMPD1 | sphingomyelin phosphodiesterase 1, acid lysosomal | −19.42 |
| RETSAT | retinol saturase (all-trans-retinol 13,14-reductase) | −26.24 |

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

The invention claimed is:

1. A cosmetic or dermopharmaceutical composition comprising a cosmetically or pharmaceutically effective quantity of the ferment extract of a strain of *Bacillus pumilus* species with deposit number LMG P-28202 and at least one cosmetically and/or dermopharmaceutically acceptable excipient and/or ingredient,
    the ferment extract having been formed by fermenting the strain of *Bacillus pumilus* species in a culture medium comprising a source of nitrogen and carbon, and separating the culture medium supernatant, containing the ferment extract, from the strain of the *Bacillus pumilus* species, and
    wherein the composition is in a formulation selected from the group consisting of creams, multiple emulsions, liquid crystals, oils, milks, balsams, foams, gels, cream gels, hydroglycolic solutions, hydrogels, liniments, soaps, shampoos, conditioners, serums, polysaccharide films, ointments, mousses, pomades, powders, bars, pencils, sprays and aerosols.

2. The cosmetic or dermopharmaceutical composition according to claim 1, wherein the ferment extract contains peptidic and glucidic material having a molecular weight of less than 7000 Da.

3. The cosmetic or dermopharmaceutical composition according to claim 1, wherein the cosmetically and/or dermopharmaceutically acceptable excipient and/or ingredient is selected from the group consisting of agents which increase the level of adiponectin in adipocytes, agents which increase the mitochondrial activity, agents which increase the ATP level in muscle, other agents stimulating healing, coadjuvant healing agents, agents stimulating reepithelialization, coadjuvant reepithelialization agents, agents which reduce the triglyceride content of adipocytes, agents delaying adipocyte differentiation, agents that reduces the amount of nocturnin, agents inhibiting the nocturnin expression, lipolytic agents or agents stimulating lipolysis, venotonic agents, agents modulating PGC-1 α expression, agents inhibiting the activity of PPARγ, anti-cellulite agents, agents which diminish the sebum production, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor clustering, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of components of the stratum corneum, ceramides, fatty acids, agents that inhibit collagen degradation, agents that inhibit matrix metalloproteinases, agents that inhibit elastin degradation, agents that inhibit serine proteases, agents stimulating fibroblast proliferation, agents stimulating keratinocyte proliferation, agents stimulating melanocyte proliferation, agents stimulating keratinocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, astringent agents, agents which inhibit the activity of PAR-2, cytokines, growth factors, agents acting on capillary circulation and/or microcirculation, agents stimulating angiogenesis, agents that inhibit vascular permeability, agents acting on cell metabolism, agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, and mixtures thereof.

4. The cosmetic or dermopharmaceutical composition according to claim 1, wherein the cosmetically and/or dermopharmaceutically acceptable excipient and/or ingredient includes at least one cosmetically and/or dermopharmaceutically acceptable excipient and/or ingredient of the group consisting of:

agents which increase the percutaneous absorption of the ferment extract; agents that reduce the triglyceride content of adipocytes, agents that delay adipocyte differentiation, anti-cellulite agents, lipolytic agents, venotonic agents, agents inhibiting PGC-1 α expression or agent inhibiting the activity of PPARγ, firming and/or redensifying and/or restructuring agents, agents stimulating the synthesis of dermal or epidermal macromolecules, anti-wrinkle and/or antiaging agents, agents stimulating healing, coadjuvant healing agents, agents stimulating reepithelialization, and coadjuvant reepithelialization agents.

5. A cosmetic or dermopharmaceutical composition comprising a cosmetically or pharmaceutically effective quantity of the ferment extract of a strain of *Bacillus pumilus* species with deposit number LMG P-28202 and at least one cosmetically and/or dermopharmaceutically acceptable excipient and/or ingredient, the ferment extract having been formed by fermenting the strain of *Bacillus pumilus* species in a culture medium comprising a source of nitrogen and carbon, and separating the supernatant of the culture medium, containing the ferment extract, from the strain of the *Bacillus pumilus* species, and wherein the ferment extract is incorporated into a sustained release system or is adsorbed on a solid organic polymer or solid mineral support, wherein the sustained release system is selected from the group consisting of liposomes, mixed liposomes, oleosomes, niosomes, ethosomes, milliparties, microparticles, nanoparticles, solid lipid nanoparticles, nanostructured lipid supports, sponges, cyclodextrins, vesicles, micelles, mixed micelles of surfactants, surfactant-phospholipid mixed micelles, millispheres, microspheres, nanospheres, lipospheres, millicapsules, microcapsules, nanocapsules, microemulsions, and nanoemulsions.

6. The cosmetic or dermopharmaceutical composition according to claim 1, wherein the formulation is selected from the group consisting of creams, multiple emulsions, foams, gels, cream gels, hydrogels, polysaccharide films, mousses, bars, and aerosols.

7. A fabric, non-woven fabric, or medical device comprising a cosmetic or dermopharmaceutical composition comprising a cosmetically or pharmaceutically effective quantity of the ferment extract of a strain of *Bacillus pumilus* species with deposit number LMG P-28202 and at least one cosmetically and/or dermopharmaceutically acceptable excipient and/or ingredient, the ferment extract having been formed by fermenting the strain of *Bacillus pumilus* species in a culture medium comprising a source of nitrogen and carbon, and separating the culture medium supernatant, containing the ferment extract, from the strain of the *Bacillus pumilus* species, and wherein the composition is in a formulation selected from the group consisting of creams, multiple emulsions, liquid crystals, anhydrous compositions, oils, milks, balsams, foams, gels, cream gels, hydroalcoholic solutions, hydroglycolic solutions, hydrogels, liniments, soaps, shampoos, conditioners, serums, polysaccharide films, ointments, mousses, pomades, powders, bars, pencils, sprays and aerosols.

8. A method of forming the composition of claim 1, comprising:

culturing the strain of *Bacillus pumilus* species in the culture medium comprising the source of nitrogen and carbon, the source of nitrogen and carbon comprisinq at least one of malt extracts and peptones.

9. The method of claim 8, wherein the culture medium further comprises at least one of exogenous sugars and yeast.

10. A method of increasing adiponectin levels, increasing mitochondrial activity in muscle, increasing muscular endurance, stimulating wound healing and/or reepithelialization of the skin, stimulating collagen synthesis and/or hyaluronic acid synthesis, treatment, hindrance and/or delay of skin aging, treatment, hindrance and/or delay of skin wrinkles, treatment of skin firming and/or hindrance, delay of loss of skin firmness, decrease in fat accumulation, decrease in body mass index (BMI), and/or increase in the strength and tone of muscle fibers, or treating inflammation, which comprises administering a composition comprising a cosmetically or pharmaceutically effective amount of a cosmetic or dermopharmaceutical composition to a subject, the composition comprising a cosmetically or pharmaceutically effective quantity of the ferment extract of a strain of *Bacillus pumilus* species with deposit number LMG P-28202and at least one cosmetically and/or dermopharmaceutically acceptable excipient and/or ingredient, the ferment extract having been formed by fermenting the strain of *Bacillus pumilus* species in a culture medium comprising a source of nitrogen and carbon, and separating the culture medium supernatant, containing the ferment extract, from the strain of the *Bacillus pumilus* species, and wherein the composition is in a formulation selected from the group consisting of creams, multiple emulsions, liquid crystals, oils, milks, balsams, foams, gels, cream gels, hydroglycolic solutions, hydrogels, liniments, soaps, shampoos, conditioners, serums, polysaccharide films, ointments, mousses, pomades, powders, bars, pencils, sprays and aerosols, the administering of the composition comprising topical or transdermal application.

11. The method of claim 10, wherein said ferment extract contains peptidic and glucidic material having a molecular weight of less than 7000 Da.

12. The method of claim 10, wherein the increase of mitochondrial activity in muscle is an increase of the level of ATP and/or citrate synthase activity in muscle.

13. The method of claim 10, wherein the increase of muscular endurance is an increase of aerobic endurance.

14. The method of claim 13, wherein the increase of aerobic endurance is an increase in the proportion of Type 1 fibers in muscle.

15. The method of claim 10, wherein the administering of the composition comprises applying the composition to at least one body part selected from the group consisting of skin and hair.

16. A method of increasing adiponectin levels, increasing mitochondrial activity in muscle, increasing muscular endurance, stimulating wound healing and/or reepithelialization of the skin, stimulating collagen synthesis and/or hyaluronic acid synthesis, treatment, hindrance and/or delay of skin aging, treatment, hindrance and/or delay of skin wrinkles, treatment of skin firming and/or hindrance, delay of loss of skin firmness, decrease in fat accumulation, decrease in body mass index (BMI), and/or increase in the strength and tone of muscle fibers, or treating inflammation, which comprises administering a composition comprising a cosmetically or pharmaceutically effective amount of the ferment extract of a strain of *Bacillus pumilus* species with deposit number LMG P-28202to a subject, wherein the ferment extract is derived by separating a supernatant, containing the ferment extract, from a culture medium containing the strain of *Bacillus pumilus* species, and wherein the administering of the composition is carried out by at least one means selected from the group consisting of iontophoresis, sonophoresis, electroporation, mechanical pressure, osmotic pressure gradient, occlusive cure, microinjections, needle-free injections by application of pressure, a microelectric patch, and a face mask.

17. The cosmetic or dermopharmaceutical composition of claim 1, wherein the source of nitrogen and carbon comprises at least one carbon and/or nitrogen source selected from the group consisting of yeast, malt extracts, and peptones.

18. The cosmetic or dermopharmaceutical composition of claim 1, wherein the extract comprises between 0.000001 weight % and 5 weight % of the composition.

19. A composition comprising a ferment extract, derived from a supernatant separated from a culture medium of a strain of *Bacillus pumilus* species with deposit number LMG P-28202, and at least one cosmetically and/or dermopharmaceutically acceptable excipient and/or ingredient selected from the group consisting of glycerol and propanediol, the ferment extract having been formed by fermenting the strain of *Bacillus pumilus* species in a culture medium comprising a source of nitrogen and carbon, and separating the supernatant of the culture medium, containing the ferment extract, from the strain of the *Bacillus pumilus*species.

20. The cosmetic or dermopharmaceutical composition according to claim 1, wherein the culture medium used in the fermentation of the strain of *Bacillus pumilus* species further includes sea salts.

21. The method of claim 16, wherein the culture medium used in the fermentation of the strain of *Bacillus pumilus* species further includes sea salts.

22. The cosmetic or dermopharmaceutical composition according to claim 17, wherein the culture medium used in the fermentation of the strain of *Bacillus pumilus* species further includes sea salts.

* * * * *